United States Patent [19]

Blakemore et al.

[11] 4,043,872
[45] Aug. 23, 1977

[54] POLYIODOTHYRONINE IMMUNOASSAY

[75] Inventors: Judith I. Blakemore, Mill Valley; Richard K. Leute, Sunnyvale; Roberta D. Ernst, Mountain View, all of Calif.

[73] Assignee: Syva Company, Palo Alto, Calif.

[21] Appl. No.: 644,408

[22] Filed: Dec. 29, 1975

Related U.S. Application Data

[63] Continuation-in-part of Ser. No. 551,566, Feb. 20, 1975, abandoned.

[51] Int. Cl.² ............................................. G01N 31/14
[52] U.S. Cl. ................................. 195/103.5 A; 195/63
[58] Field of Search ................... 195/103.5 R, 103.5 A

[56] References Cited

U.S. PATENT DOCUMENTS

| 3,817,837 | 6/1974 | Rubenstein et al. | 195/103.5 R |
| 3,850,752 | 11/1974 | Schuurs et al. | 195/103.5 R |

Primary Examiner—Alvin E. Tanenholtz
Assistant Examiner—C. A. Fan
Attorney, Agent, or Firm—Townsend and Townsend

[57] ABSTRACT

Method and enzyme conjugates are provided for determining physiological amounts of polyiodothyronine in physiological fluid, particularly serum.

A homogeneous enzyme immunoassay is provided employing an enzyme-bound-polyiodothyronine having less than about 50 percent of the original enzyme activity, whose activity increases upon binding with a receptor. The enzyme-bound-polyiodothyronine, the unknown suspected to containing a polyiodothyronine, and receptor for the polyiodothyronine are combined in an aqueous medium containing substrate for said enzyme and the enzymatic activity of the solution determined. By comparing the result obtained with results obtained from standards having known amounts of polyiodothyronine, the amount of polyiodothyronine in the unknown can be determined.

The enzyme-bound-polyiodothyronine employs an enzyme which is reversibly deactivated by polyiodothyronine, so as to be reactivated by receptor binding to the polyiodothyronine. Particular enzymes include malate dehydrogenase and triose phosphate isomerase.

12 Claims, No Drawings

POLYIODOTHYRONINE IMMUNOASSAY

CROSS-REFERENCE TO RELATED APPLICATION

This application is a continuation-in-part of application Ser. No. 551,566, filed Feb. 20, 1975, now abandoned.

BACKGROUND OF THE INVENTION

1. Field of the Invention

The concentration of thyroxine in the bloodstream is within relatively narrow limits critical to the proper functioning of the body. The concentration of thyroxine is extremely small and can only be detected in very sensitive techniques.

One technique which is employed for the determination of thyroid hormones is radioimmunoassay. While this technique has many variations, it employs the combination of an antibody for the thyroid hormone and radioactive or hot thyroid hormone with blood serum and a separation of the bound hormone from unbound hormone. The amount of hot hormone, which is bound to antibody or remains free, will be a function of the amount of hormone in the serum. By determining the radioactivity of the solution freed from antibody, one can calculate the amount of hormone based on standards employing known amounts of hormone.

The use of radioimmunoassay requires a separation step which introduces errors and can be time-consuming. In addition, one must work with radioactive materials which decay and, therefore, have a limited shelflife. Also, working with radioactive materials is generally undesirable because of health hazards. There is a continuing need for a simple technique which minimizes the manipulative steps, while providing a high degree of sensitivity.

2. Brief Description of the Prior Art

U.S. Pat. No. 3,817,837 describes an enzyme assay which is found to be generically useful for a wide variety of ligands.

SUMMARY OF THE INVENTION

A homogeneous enzyme immunoassay technique is employed for the determination of thyroid hormones. The enzyme reagent employed in the immunoassay is an enzyme-bound-polyiodothyronine (EBP), employing an enzyme which upon conjugation to a polyiodothyronine is more than about 50 percent deactivated and upon binding of receptor for the polyiodothyronine, is partially or completely reactivated. Thus, the conjugated enzyme which is employed has a low turnover rate, which is substantially increased in the presence of receptor, for example, antibody for polyiodothyronine.

The assay is carried out by combining in an aqueous buffered medium a serum sample to be measured, the appropriate receptor, EBP, and the enzyme substrates, and determining the rate of the enzyme catalyzed reaction. One or more incubation periods may optionally be included between reagent additions. By preparing standards having known amounts of T-4, a calibration curve can be prepared to which unknown samples may be related.

The EPB compositions have on the average at least one polyiodothyronine bonded to the enzyme through an aliphatic carbon atom or non-oxo-carbonyl group (including nitrogen and thio-analogs thereof) forming an amide (amidine or thioamide respectively) and/or ester.

DESCRIPTION OF THE SPECIFIC EMBODIMENTS

A method and compositions are provided for determining polyiodothyronines (T-4) at concentrations as low as $10^{-7}$M or lower, which is a homogeneous enzyme immunoassay. By analogy to the invention described in U.S. Pat. No. 3,817,837, T-4 is the ligand, enzyme-bound-ligand is enzyme-bound T-4 and antiligand is antibody for T-4. Particularly, the enzymes are malate dehydrogenase or triose isomerase.

The homogeneous enzyme immunoassay of this invention employs as reagents enzyme-bound-polyiodothyronine, particularly T-4, receptor for polyiodothyronine, particularly antibody, e.g., anti-T-4, substrates for the enzyme and an aqueous, normally alkaline, buffer medium, usually having one or more additives for enhancing enzyme stability, for measuring the product of the enzyme reaction, or the like. The order of the addition of the reagents to the aqueous assay medium is not critical, although particular protocols will be preferred. In addition, incubation may be desirable after the addition of particular reagents.

After all the reagents have been added, the rate of reaction for the enzyme will be followed, normally spectrophotometrically. By comparing the result obtained with the unknown to results obtained employing known amounts of the polyiodothyronine, the amount of polyiodothyronine in the unknown can be determined.

The order of description of this invention will be a description of the reagents first, followed by a description of the assay.

REAGENTS

Enzyme-Bound-Polyiodothyronine

In preparing the enzyme-bound-polyiodothyronine, one may use the polyiodothyronine directly, activating the carboxyl group to be bound to available groups on the enzyme, e.g., lysines and tyrosines, or preferably, provide an extended chain from the available functionalities such as the amino group or the carboxy group, particularly the amino group. The phenolic hydroxyl group will not be used as a site for conjugation.

The enzymes which find use are those which are substantially reversibly deactivated upon conjugation of a polyiodothyronine, so that upon binding to an antibody for polyiodothyronine, substantial activity is recovered. Only a select group of enzymes are found to have this activity, particularly malate dehydrogenase, more particularly mitochrondrial, preferably pig heart mitochrondrial malate dehydrogenase (MDH) and triose phosphate isomerase, particularly rabbit muscle triose isomerase (TIM). Usually, the polyiodothyronine will be bound to the enzyme by a linking group which is linked to the amino group of the polyiodothyronine, with the carboxy group esterified, particularly with a lower alkyl group, usually of from one to three carbon atoms. Conveniently, the polyiodothyronine may be bonded through a functional group which has two non-oxo-carbonyl functionalities. (For the purposes of this invention, non-oxo-carbonyl shall mean the oxygen containing carboxy

the nitrogen containing imidic group

the sulfur containing thionocarboxy

and the derivatives thereof, e.g., amides, esters and anhydrides.)

The number of polyiodothyronines conjugated to the enzyme on the average will be at least one and not more than about ten per enzyme, usually two to six. The polyiodothyronines may be joined to available sites, e.g., amino or hydroxy to form amides and esters, by any convenient linking group from the amino group or carboxy group, particularly the amino group, of the polyiodothyronine. Since the amino group will have to be protected during conjugation, when the carboxyl group is involved in the conjugation, for the most part linking groups will be attached to the amino site. Conveniently, the ester of the polyiodothyronine will be employed and a group having a non-oxo-carbonyl functionality (see the above definition) will be employed for conjugation to amino and hydroxyl groups of the enzyme.

A bond or linking group may join the polyiodothyronine to the enzyme. The particular linking group has been found not to be critical to this invention, although certain classes of linking groups are preferred. The number of atoms in the linking group other than hydrogen will generally be not more than 20, usually not more than 16, and may have from 0 to 7, usually 1 to 6 heteroatoms, particularly chalcogen (O and S), normally bonded solely to carbon, and nitrogen, being bonded solely to carbon and hydrogen and being neutral when bonded to hydrogen e.g. amido.

The particular enzyme which is employed is one which is reversibly deactivated by a polyiodothyronine, so that in the absence of receptor for polyiodothyronine, the enzyme has less than about 50 percent, usually less than about 35 percent, and more usually less than about 25 percent of the original enzyme activity present prior to conjugation, retaining at least 0.5, usually at least 1 percent of the original enzyme activity present prior to conjugation. Upon introducing an excess of receptor for polyiodothyronine to the enzyme conjugate, the enzymatic activity will increase by at least 50 percent, more usually at least 100 percent, and frequently by 200 percent or more. The amount of increase in activity will depend to a substantial degree on the original decrease in activity upon conjugation. Other enzymes, particularly dehydrogenases, which are found to be inhibited by thyroxine are reported in Wolff and Wolff, Biochimica et Biophysica Acta, 26, 387 (1957). These enzymes include glutamic dehydrogenase, lactate dehydrogenase, yeast alcohol dehydrogenase, yeast glucose-6-phosphate dehydrogenase and glyceraldehyde-3-phosphate dehydrogenase.

Generically, the EBP will have the following formula:

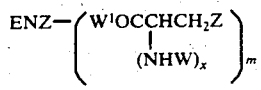

wherein

ENZ is an enzyme which is reversibly inhibited by a polyiodothyronine, particularly T-4, so that the enzyme is activated when the polyiodothyronine is bound by receptor e.g. antibody; the enzyme will generally be a dehydrogenase or triose phosphate isomerase $x$ is 0 or 1

Z is

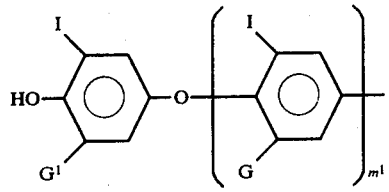

wherein:

$m^1$ is 0 or 1;

G and $G^1$ are iodo, one of W and $W^1$ is a linking group, preferably aliphatic, having from 0 to 1 site of ethylenic unsaturation, of from 1 to 20 atoms other than hydrogen, which are carbon, chalcogen, and nitrogen, chalcogen being bonded solely to carbon as oxy or oxo (including thio analogs), particularly non-oxo carbonyl, and nitrogen being bonded solely to carbon and hydrogen and being neutral when bonded to hydrogen e.g. amido; the number of heteroatoms usually being in the range of 1 to 8, more usually in the range of 2 to 7, and preferably 2 to 4; there normally being not more than 5, usually not more than 4, and preferably 2 to 3 functionalites in the linking group chain e.g. tert.-amino, oxy, amido, etc., with the proviso that $W^1$ may be a bond, particularly when $x$ is 0;

when other than a linking group, W is hydrogen and $W^1$ is hydroxyl or alkoxyl of from 1 to 3 carbon atoms, particularly methyl; and $m$ is on the average at least 1 and not more than 10, usually 1 to 8, more usually 2 to 6.

The EBP employed in this invention will for the most part have the following formula

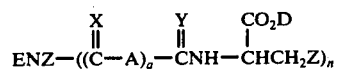

wherein

ENZ is an enzyme which is reversibly inhibited by a polyiodothyronine, particularly T-4, so that the enzyme is activated when the polyiodothyronine is bound by receptor; the enzyme will usually be a dehyrogenase, particularly malate dehydrogenase, or triose phosphate isomerase.

$n$ is on the average at least one, and not more than 10, usually 1 to 8, more usually 2 to 6;

$a$ is 0 to 1, usually 1;

X and Y are the same or different and are chalcogen (O or S) or imino (=NH), normally Y will not be imino;

D is hydrogen or an alkyl group of from 1 to 6 carbon atoms; usually 1 to 3 carbon atoms, and preferably 1 carbon atom;

Z is 3,3',5,5'-tetraiodo-4-(hydroxyphenoxy-1')-phenyl-1 or 3,5-diiodo-4-hydroxyphenoxy; and A is a bond or an organic divalent group of at least one carbon atom, usually at least two carbon atoms, and usually not more than 12 carbon atoms, more usually not more than 10 carbon atoms having from 0 to 12, usually 1 to 10, more usually 2 to 9, and preferably 3 to 7 atoms in the chain (with cyclic groups the greater number of annular atoms will be included) between the non-oxo-carbonyl groups and having from 0 to 4, usually 0 to 1 to 3, more usually 1 to 2 heteroatoms in the chain, which may be chalcogen (O or S) (as oxy, thio or sulfonyl) or nitrogen (tertiary amino or amido); the total number of heteroatoms will be from 0 to 6, generally 0 to 5, usually 0 to 1 to 4, more usually 1 to 3, which will be chalcogen (O or S) (as non-oxo-carbonyl, non-oxothiocarbonyl, oxy, thio or sulfonyl) or nitrogen (imino, tertiary amino or amido); there usually being two carbon atoms between heteroatoms in the chain.

A may be hydrocarbylene (aliphatic, alicylic, aromatic or combinations thereof) or non-hydrocarbylene (substituted aliphatic, alicyclic, aromatic, heterocyclic or combinations thereof), generally having from 0 to 1 cyclic group in the chain, normally of from 5 to 6 annular members having from 0 to 2 heteroannular members, usually 0 to 1 heteroannular member, the cyclic group will usually have substituents separated by from 2 to 4, usually 3 to 4 annular members; normally the hydrocarbylene will have as its only aliphatic unsaturation from 0 to 1 ethylenic groups, and is preferably saturated, particularly preferred is alkylene having from 0 to 1 carboxamido, imino, or oxy group in the chain. When A is carbocyclic aromatic, A will usually have 6 to 10, more usually 6 to 8 carbon atoms.

The total number of functional groups in the chain (oxy, amino, amido and sulfur and nitrogen analogs thereof) will generally be from 0 to 4, usually 0 to 3, and more usually 0 to 1 to 2.

Included within the compound genus are ENZ-bound-T-4 compositions which have a di-non-oxo-carbonyl link having an aliphatic chain which is uninterrupted by heteroatoms or interrupted by from about 1 to 2 heteroatoms, chalcogen and nitrogen. These compounds will for the most part have the following formula:

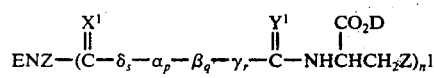

Enz, D and Z have been defined previously;

$n^1$ has the same limits as $n$, but is on the average, 1 to 10, preferably 1 to 8, and more preferred 2 to 6;

$X^1$ and $Y^1$ have the same limits as X and Y respectively, with $X^1$ normally being chalcogen, and $Y^1$ preferably being oxygen;

$p$, $q$ and $r$ are each 0 to 1, with the total of $p$, $q$ and $r$ preferably equal to at least one ($p + q + r \geq 1$);

$s$ is 0 to 2, usually 0 to 1;

$\alpha$ and $\gamma$ are hydrocarbon groups of from 1 to 8, usually 1 to 6 carbon atoms, more usually of from 1 to 3 carbon atoms, having a total of from 1 to 12 carbon atoms, usually a total of from 2 to 10 carbon atoms, preferably a total of from 2 to 8 carbon atoms, and more preferred a total of from 2 to 6 carbon atoms; where $p$ or $r$ is 0, $\alpha$ or $\gamma$ is preferably of from 1 to 8 carbon atoms, more preferably of from 1 to 6 carbon atoms; $\alpha$ and $\gamma$ may be aliphatic, alicyclic, aromatic or heterocyclic and together with $\beta$ and $\delta$ come within the definitions of A; preferably $\alpha$ and $\gamma$ are saturated aliphatic, particularly unbranched, e.g., methylene or polymethylene or aromatic, particularly monocyclic, where only one of $\alpha$ and $\gamma$ are aromatic;

$\beta$ is oxy (—O—), thio (—S—), sulfonyl (—SO$_2$—) or amino

where T is alkyl of from 1 to 6 carbon atoms, usually 1 to 3 carbon atoms or hydrogen; when $\beta$ is bonded to non-oxo-carbonyl, ($p$ is 0) normally $\beta$ will be amino or alkylamino; and

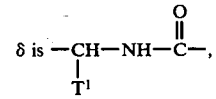

wherein $T^1$ is hydrogen or lower alkyl of from 1 to 3 carbon atoms.

In a preferred subgenus, the polyiodothyronine may be combined with a dibasic dicarboxylic acid to form an amic acid (the monoamid of a dibasic acid). The dibasic acid will normally be of from 2 to 8 carbon atoms, usually 2 to 6 carbon atoms, have from 0 to 1 site of ethylenic unsaturation in the chain, and have from 0 to 1 atoms of atomic number 7 to 8 (nitrogen or oxygen), any nitrogen or oxygen being bonded solely to carbon, i.e. tertiary amino or ether. Preferred dibasic acids form cyclic anhdrides of from 5 to 7, particularly 5 to 6 annular members. In order to insure that the carboxyl group of the dibasic acid conjugated to the thyronine is the one that reacts with the ENZ, the original carboxyl group of the thyronine will normally be esterified with an alkyl group of from 1 to 3 carbon atoms, preferably 1 carbon atom (methyl).

The modified polyiodothyronine or its analog which is employed for conjugation with ENZ will for the most part have the following formula:

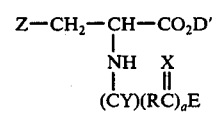

wherein:

X, Y, Z and $a$ are as defined previously;

D' is hydrogen or alkyl of from 1 to 3 carbon atoms, preferably one carbon atom;

R has the same definition as A, but is preferably an aliphatic divalent group having from 0 to 1 site of ethylenic unsaturation and from 0 to 1 heteroatom of atomic number 7 to 8, the heteroatoms being completely substituted by carbon atoms, and is of from 1 to 6 carbon atoms; and E is hydroxyl, or may be taken together with a terminal nitrogen of R to form a double bond, e.g., isocyanate or isothiocyanate.

Another convenient series of compounds has a carbocyclic or heterocyclic ring of from 5 to 6 annular member in the chain, the heterocyclic ring having from 1 to 2, usually one heteroannular member, which is O, S or N. Preferably, these compounds have an isocyanate or isothiocyanate bonded directly or indirectly to an annular member, particularly where the ring is aromatic. For the most part these compounds will have the following formula:

wherein:
D and Z have been defined previously;
$X^2$ and $Y^2$ are chalcogen (O or S), preferably $X^2$ is S;
Ar is arylene or aralkylene, including carbocyclic and heterocyclic of from 5 to 6 annular members, having from 1 to 2, preferably 1, heteroannular members, which are O, N and S and is of from 4 to 10 carbon atoms, usually 4 to 8 carbon atoms and when heterocyclic, preferably 4 to 6 carbon atoms, and when carbocyclic, preferably 6 to 8 carbon atoms.

The ENZ conjugate of the above series of compounds will have the formula:

wherein all the symbols have been defined previously.

The polyiodothyronine analog will be employed in an active or activated form, so as to be capable of reacting with available non-oxo-carbonyl reactive groups of ENZ, e.g. amino and hydroxyl.

For the carboxy, a mixed anhydride, a N-hydroxy succinimide, p-nitrophenyl, phenylthio, etc., ester derivative or a carbodiimide coupling reagent is conveniently employed, while imidate esters and isothiocyanates are employed directly for conjugation with ENZ. The reaction is carried out at moderate temperatures generally in the range of about −5 to 30° C in a mixed aqueous buffered medium, usually at a mildly alkaline pH, generally in the range of about 7 to 10. A co-solvent may be employed, e.g. hexamethylphosphoramide. The co-solvent when employed will generally be used in amounts of about 10 to 40 percent, preferably from about 20 to 30 volume percent.

The mole ratio of T-4 analog to ENZ molecules will generally vary from about 1:1 to 20:1, more usually from about 3:1 to 10:1.

The T-4 analog may be added incrementally or in bulk and the reaction time will generally vary from about 1 minute to about 48 hours. At the end of this time, the reaction mixture may be worked up according to conventional techniques. Preferably, the mixture is chromatographed, so as to separate any unreacted analog from the ENZ-bound-T-4. A convenient chromatographic material is Sephadex. The fractions may be isolated, their enzyme activity determined, and those fractions having enzyme activity pooled.

Rather than an analog formed by combining the polyiodothyronine with a di-non-oxo-compound, desamino-T-4 may be conjugated to ENZ. With the polyiodothyronine, the amino group must be protected when conjugating ENZ with the amino acid, while with the desaminopolyiodothyronine, no protective group is required and the carboxy group may be activated in the same manner as the other carboxy groups.

The desaminopolyiodothyronine or its monocyclic analog will come within the following formula:

where Z has been defined previously, and $t$ is 0 or 1;
while the ENZ conjugate of these compounds will have the following formula

wherein all the symbols have been defined previously.

The ENZ-bound-T-4 will normally be at least about 50 percent deactivated in comparison to the enzyme activity present prior to conjugation, usually at least about 65 percent deactivated and not more than about 99.5 percent deactivated. Desirably, the enzyme would be almost completely deactivated and its activity substantially completely restored upon addition of excess anti-T-4. However, it is found that the conjugated enzyme is activated by binding to receptor to from about 5 to 60% of the original activity of the unconjugated enzyme, usually from 10 to 50% of the original activity of the unconjugated enzyme. The primary concern is the spread in measured units between ENZ-bound-T-4 in the absence of antibody and in the presence of excess antibody. By excess is intended sufficient antibody to bind substantially all the available T-4.

The enzyme is conveniently mitochrondrial pig heart malate dehydrogenase or rabbit muscle triose phosphate isomerase.

Anti-T-4

The appropriate antibodies are produced by the injection of a T-4-bound-antigen into a vertebrate, usually a domestic animal, e.g. sheep, rabbit or goat. Since the antigen is normally a polypeptide or protein, normally of from about 5,000 to 10 million molecular weight, the conjugated antigen will be formed by the combination of a T-4 analog and the antigenic polypeptide or protein. Either the same or different analog may be used from the analog employed for the conjugation with ENZ. Besides the analogs employed for preparing the conjugate, other analogs may be employed. In addition, thyroglobulin may be employed for the production of antibodies.

Depending upon the particular analog which is employed, various techniques which have been described in the literature may be used for the preparation of the antigens. The antigens will have at least one analog molecule and, preferably, from about 1 per 2,000 molucular weight of the antigen to about 1 per 50,000 molecular weight of the antigen. The ratio T-4 analogs to molecular weight will increase with the decreasing molecular weight of the antigen.

The injection of the antigen into the animal will follow conventional techniques, although it may be preferable to use complete Freund's adjuvant with the booster injection.

A wide variety of proteins may be employed as antigens, such as albumins, globulins, keyhole limpet hemocyanin, and the like.

Buffer

The buffers employed may be widely varied and include phosphate, carbonate, glycinate, Tris, and the like. Phosphate should not be employed in high concentrations, <0.1M. One buffer may be preferred over another buffer, with glycinate or triethanolamine being the preferred buffers.

Other Additives

Depending upon the course of reaction, the substrates for MDH will be malate and NAD or oxaloacetate and NADH. For triose phosphate isomerase (TIM) the enzymatic reaction of the enzyme is coupled with a second enzyme to allow for spectrophotometric determination. Therefore, included in the assay medium is the substrate for TIM, glyceraldehyde phosphate, NADH, and alpha-glycerophosphate dehydrogenase. The latter enzyme and NADH are used in substantial excess, so as not to be rate limiting.

Advantageously, a small amount of ethylenediaminetetraacetic acid is included to reduce bacterial growth and sequester heavy metals. A protein and glycerol may also be included in the assay medium to enhance enzyme stability. Additional stabilizers such as dithioerythritol or other antioxidants may also be included. Also, small amounts of sodium azide may be added as a preservative.

ASSAY

Reagent Solutions

The buffer solution employed will normally be at a concentration to provide in the assay medium a concentration of from about 0.001 to 0.5M, usually from about 0.01 to 0.2M, and preferably from 0.05 to 0.15M. The protein which is included, which is conveniently an albumin, such as rabbit serum albumin and/or gelatin, will generally be present in about 0.005 to 0.5 weight percent in the final assay mixture, more usually from about 0.01 to 0.2 weight percent. Glycerol may be present in from 0.1 to 5, usually 0.4 to 4 weight percent. The pH of the solution will generally be from about 6.0 to 10.5, usually from about 7 to 10.5, and more usually about 8 to 10, and preferably from 8.5 to 10.5 when NAD and malate or NADH and oxaloacetate are employed, and preferably from 7 to 9 when glyceraldehyde phosphate is employed.

In the assay medium, the concentration of ENZ may be varied widely, but will generally be in the range of about $10^{-5}$ to $10^{-12}$M, more usually from about $10^{-7}$ to $10^{-11}$M. The antibody concentration will be based on a ratio of antibody binding sites to the concentration of polyiodothyronines bound to the ENZ. Generally, the ratio of binding sites to T-4 as ENZ-bound-T4 will be at least 0.5 and not greater than 1000, more usually being from about 1 to 100, and most usually from about 1 to 25. Usually sufficient antibody is added to recover from 25 to 75, preferably 25 to 50% of the recoverable enzyme activity.

Increased amounts of antibody will be required with decreasing binding constants. The specific amount of antibody employed in a specific assay will normally be determined empirically.

Other minor additives which may be added include ethylenediaminetetraacetic acid, which may be present in from about 0.001 to 0.1 weight percent, sodium azide which may be present in from about $10^{-5}$ to $10^{-3}$M and a surfactant such as Triton X-100 which may be present in from about 0.0001 to 0.03 weight percent.

When employing MDH, depending on the direction of the reaction, either malate and NAD or oxaloacetate and NADH will be employed, the former being preferred. The concentration of these materials directly affects the assay sensitivity and must be determined empirically so as to optimize the difference in the rate of the reaction in the presence and in the absence of added antibody. The concentration of malate or oxaloacetate will generally be from about 0.01 to 0.5M, more usually from about 0.05 to 0.3M. The concentration of NAD or NADH will generally range from about 0.001M to 0.05M, more usually from about 0.005M to about 0.2M. Normally, the concentrations of the enzyme, antibody, and substrates are chosen to optimize the sensitivity of the assay.

When TIM is employed, the glyceraldehyde phosphate will generally be at a concentration in the range from about $10^{-1}$ to $10^{-4}$M, alpha-glycerophosphate dehydrogenase will generally be present in amounts of $10^{-5}$ to $10^{-9}$M, while NADH concentrations will generally be from about $10^{-2}$ to $10^{-4}$M.

The various reagents can be conveniently added as aqueous solutions. Normally, a large proportion of the total assay sample will be the buffer solution.

Assay Steps

The order of combination of the various reagents is not critical, although some orders are preferred and in some instances, one order will be preferred over another. Incubation may be employed after the addition of any particular reagent or after all the reagents have been combined. Usually, the assay mixture will not be incubated in the presence of the enzyme substrates for more than 10 minutes prior to beginning the rate measurement.

All of the reagents may be combined simultaneously. Alternatively, the sample, e.g. serum, buffer and antibody may be combined, optionally followed by incubation. In most instances, antibody and the conjugated ENZ will not be combined prior to addition of the sample. However, when monovalent antibody is employed so as to avoid precipitin formation, it may for certain applications be desirable to store a mixture of the antibody and enzyme.

Depending on the order of addition, the events that occur will be different. If the sample and antibody are combined, the polyiodothyronine will bind to the antibody and reduce the number of available sites for binding to the ENZ-bound-T-4. The concentration of available binding sites will therefore be a function of the amount of T-4 in the sample. When the ENZ-bound-T-4 is added, the amount of antibody that binds to the conjugated or T-4 will be a function of the T-4 in the sample. This procedure is less sensitive to differences in binding constants between T-4 and ENZ-bound T-4.

Alternatively, one can combine the sample, the appropriate antibody and the conjugated ENZ and allow the free T-4 to compete with the T-4 conjugated to ENZ for available binding sites.

Optionally, the assay mixture may be incubated after each addition of a reagent, either before or after addition of the enzyme substrates or other reagents. Incubation may vary from 2 minutes to 1 hour, and will generally be at temperatures in the range of about 15° to 40° C, usually about 25° (ambient) to 37° C.

After addition of the mixture to the substrates for the enzyme, the mixture may be incubated for up to about 10 minutes prior to an initial reading which may be done employing either a flow cell or a cuvette. The rate is determined at a temperature in the range of about 20° to 40° C, more usually from about 25° to 37° C. Generally, readings will be of a duration of from about 0.1 to 45 minutes, usually 0.5 to 2 minutes, when a flow cell is used, and 5 to 45 minutes when a cuvette is used. Measurement periods of 5–20 minutes are useful for certain automated instruments.

By employing standards having known amounts of T-4 in serum, one can establish a calibration curve which can be used for the determination of the amount of T-4 present in an unknown.

While spectrophotometric techniques are most convenient for following the course of the enzyme reaction, namely following the absorption spectrum, other techniques may also be employed such as fluorimetry, titrimetric, etc.

The following examples are offered by way of illustration and not by way of limitation.

EXPERIMENTAL (All temperatures not otherwise indicated are in Centigrate. All percents not otherwise indicated are by weight.)

EXAMPLE I N-Methyl, N-carboxymethylglycyl Thyroxine Methyl Ester ($T_4$-MEMIDA)

Into a 25 ml flask equipped with stirrer and septum stopper was charged 1.054g (1.27 × $10^{-3}$mole) of the methyl ester of thyroxine hydrochloride. The thyroxine ester hydrochloride was dissolved under an argon blanket in 8ml of dimethyl formamide (DMF) to which was added 10ml of dry tetrahydrofuran (THF), followed by the addition of 253μl of dry triethylamine.

After stirring the mixture for 15 minutes, 0.279g (2.16 × $10^{-3}$mole) of N-methyl iminodiacetic acid anhydride in 2.5ml of dry THF was added in one addition. The reaction appeared to occur instantaneously. Volatiles were removed in vacuo on a rotary evaporator to leave a foamy solid which was dissolved in 25ml THF and the THF solution extracted with a combination of 30ml of deionized water and 50ml of ethyl acetate. After extraction and separation, the aqueous layer was extracted three times with 25ml portions of ethyl acetate. The organic layers were then combined, extracted once with 50ml of saturated NaCl solution and then dried with anhydrous magnesium sulfate. After suction filtration of the organic layer, the solvent was removed on a rotary evaporator to yield a white solid which was dissolved in 30ml of THF. To the THF was added 35ml of chloroform, the solution heated to reflux, and n-heptane added slowly. The volume of the solution was reduced until a definite cloud persisted. The solution was allowed to cool at room temperature, followed by cooling in a freezer, to yield a white fluffy product, which was washed with 1-hexane, and dried in vacuo over phosphorus pentoxide to yield 1.26g (75%) of a fluffy white product.

EXAMPLE II Conjugation of $T_4$-MEMIDA to Bovine Serum Albumin (BSA)

To a reaction vessel equipped with stirrer and septumed glass stopper was charged 0.10g (1.09 × $10^{-4}$mole) of $T_4$-MEMIDA and 0.013g (1.1 × $10^{-4}$mole) of N-hydroxysuccinimide. To the reaction vessel under an argon blanket was added one ml of dry THF followed by the addition of 15μl of dry triethylamine. After cooling the mixture in an ice bath to 0°, 0.024g (1.25 × $10^{-4}$mole) of 1-ethyl-3-(3'-dimethylaminopropyl) carbodiimide hydrochloride (ECDI) was added as a powder. The mixture was stirred for 2 hours at 0° followed by 12 hours at 4°. A solution was prepared of 0.100g (1.55 × $10^{-6}$mole) of BSA in 3.0ml of sodium bicarbonate-carbonate buffer, pH 9.4, and the pH readjusted to 9.5 with 6N sodium hydroxide. The BSA solution was cooled to 0° and the previously prepared $T_4$-MEMIDA ester solution added dropwise at a rate of 50μl per minute with vigorous stirring. The mixture was then stirred for 1.3 hours at 0°, followed by stirring gently for 2 days at 4°.

To the solution was then added dropwise a 3M hydroxylamine hydrochloride solution neutralized to pH 8.9 with 6N sodium hydroxide. After stirring the mixture for 10 hours at 4°, the mixture was placed in a dialysis bag and dialyzed against two 500ml portions of Tris-HCl buffer (0.05M, pH 7.8) for one day. The volume of the protein mixture was then concentrated to 25ml with Aquacide II (avaialble from Calbiochem) and twice subjected to gel filtration chromatography, using each time, freshly packed Sephadex G-15, initially swollen in Tris-HCl buffer, 0.1M, pH 9.0. The column size was 2.6 × 22.2cm, the flow rate was 48 drops per minute, 40 drop fractions were collected, and the buffer of elution was Tris-HCl, 0.1M, pH 9.0. The protein fractions were pooled and dialyzed against deionized water (5 × 2,000ml portions) for 3 days. The conjugate solution was then lyophilized to yield 0.15g of a white fluffy solid which was dried in vacuo over $P_2O_5$ for 3 days to yield 0.140g of conjugate. Ultraviolet analysis indicated that 22 haptens were bound to each molecule of BSA.

EXAMPLE III Carboxymethoxyacetyl Thyroxine Methyl Ester (DGMA)

To a solution of 1.65g of the methyl ester of thyroxine hydrochloride in 80ml of dry THF and 30ml of chloroform in a flask protected from light was injected 300μl of triethylamine while the mixture was agitated. Diglycolic anhydride (255mg, 0.0022 mole) was then added and the mixture stirred overnight. The solution was then washed 3 times with water, dried over sodium sulphate and the volatiles removed in vacuo. The residue was purified on a 30g Sephadex LH-20 column, using a solution of 20% methanol in dichloromethane as eluent. The clear fractions were collected, the solvent removed and the residue precipitated from methanol with water, yielding 1.53g, 84 percent.

EXAMPLE IV DGMA Conjugate to Bovine Serum Albumin

To a solution of 100mg BSA in 30ml aqueous 8M urea at 0° was added slowly 25ml of DMF, followed by the dropwise addition of 453 mg (5.9 × $10^{-4}$mole) DGMA in 5ml DMF. At completion of the addition, the pH of the reaction mixture was adjusted to 4.5 and 100mg (0.0005m) of ECDI hydrochloride was added in 10mg portions at half-hour intervals to the stirring solution maintained at 0°. At the end of 5 hours, the reaction mixture was adjusted to pH 9 and dialyzed against 2 liters of 10% DMF in 4M urea, pH 9. The precipitate was spun down and the supernatant dialyzed in a Dow Beaker Dialyzer against 25 gallons of 0.05M carbonate, pH 9, followed by 5 gallons of ammonia water, pH 9. Lyophilization afforded 95mg of conjugate which was shown by UV analysis to have 23 DGMA groups per BSA molecule.

EXAMPLE V Methyl Methoxycarbimidomethoxyacetyl Thyroxinate Conjugate to BSA

A. To a suspension of 125mg (1.1 mole) cyanomethoxyacetic acid in 1ml dichloromethane was added 98µl oxalyl chloride (146mg, 1.15 mmole). One drop of dimethylformamide was added to initiate the reaction and the reaction mixture was stirred fo 30 minutes until cessation of the effervescence and dissolution of the acid starting material. The solvent was then stripped off on the Rotavap and the remaining yellow oil added to a suspension of 827mg (1 mmole) methylthyroxinate hydrochloride in 10ml dry tetrahydrofuran containing 280µl triethylamine (2 mmole). The reaction was ended after 2 hours when analytical thin-layer chromatography (silica gel, 25% ethyl ether in chloroform) showed no remaining thyroxine ester starting material. The reaction mixture was poured into water overlaid with ethyl acetate and the aqueous layer extracted three times with 50ml of ethyl acetate. The organic layers were combined, washed once with water, once with brine, dried over magnesium sulfate and evaporated in vacuo to yield 888mg (quantitative) of a pale yellow foam. Chromatography on Sephadex LH-20 (25g, 10% methanol in ethyl acetate) provided removal of a polar impurity. Yield, 85 percent.

B. A solution of 89mg of methyl cyanomethoxyacetyl thyroxinate (0.1 mmole) in 1ml of dry methanol was placed in a dried, nitrogen-purged flask equipped with a serum stopper. A solution of sodium methoxide in methanol was added (1.1 equivalents of base) and the reaction stirred overnight in the dark. After 20 hours, thin-layer chromatography (25% ethyl ether in dichloromethane, silica gel) showed essentially complete reaction with some colored impurities.

C. A solution of the above imidate (0.1 mmole) in 2ml of basic methanol (the untreated imidate formation reaction mixture) was added dropwise to a solution of 112mg bovine serum albumin (~0.1 mmole lysine) in 5ml of 0.05M Tris buffer at pH 8.5. The pH of the reaction mixture was adjusted to pH 9.5 with 0.5M hydrochloric acid and the reaction mixture stirred in the cold for 24 hours. The mixture was dialyzed against 10 l. of dilute sodium bicarbonate solution and 3 l. of deionized water. Analysis by ultraviolet spectroscopy indicated a conjugation number of approximately 20, based on an experimentally determined extinction coefficient for thyroxine of $6.2 \times 10^3 M^{-1} cm^{-1}$. Sephedex G-15 gel filtration (0.05M Tris, pH 9 eluent) produced no change in the conjugation number.

EXAMPLE VI (N-Carboxymethyl 3-Aza-3-methylglutaramic Acid Amide of Methyl Thyroxinate) Conjugate to MDH A. To a stirred solution of 0.201g (0.22 mmole) $T_4$-MEMIDA, 1ml dry THF, 25 mg (0.22 mmole) N-hydroxy succinimide and 30µl dry triethylamine at 0° was added 0.048g(0.25 mmole) of ECDI. The mixture was stirred for 35 minutes at 0°, then for 14 hours at 4°.

To 0.033g (0.44 mmole) of glycine in 1.5ml deionized water and 0.5ml pyridine adjusted to pH 9 with 1N NaOH at 0° was added dropwise the above solution with vigorous stirring. After continued stirring at 4° for 36 hours in the dark, the solvent was removed in vacuo and the residue dissolved in 5ml abs. ethanol, and the ethanol evaporated, the ethanol treatment being repeated three times to yield a white foamy solid.

The residue was dissolved in 10ml methanol, which was poured into 15ml deionized water and extracted with 3 portions 25ml each of ethyl acetate. The ethyl acetate layers were combined, extracted with 25ml saturated brine and then dried over $MgSO_4$.

Volatiles were removed in vacuo, the residue dissolved in 2ml methanol and chromatographed on silica gel ($Et_3N:CH_3OH:CH_2Cl_2$ 31-2.1:10:90). The product was deadsorbed with $CH_3OH/CH_2Cl_2$, 1:1, the mixture filtered, the volatiles evaporated, and the residue dissolved in 5ml THF and filtered again. After removal of volatiles, the residue was taken up in THF and recrystallized from $THF/HCCl_3$/cyclohexane to yield 0.046g, 21.6%.

B. Into a 1ml vessel was charged 4.9mg radioactive $C^{14}$ N-carboxymethyl 3-aza-3-methylglutaramic acid amide of methyl thyroxinate, dissolved in 39µl DMF and cooled to 4°. To the DMF solution with stirring was added 51µl of a 0.11M ECDI solution in DMF at 4° and 10µl of 0.5M N-hydroxy succinimide in DMF at 4° and the mixture stirred overnight in the dark.

C. Pig heart mitochondrial MDH was dialysed against 0.05M carbonate buffer, pH 9.0, to yield 4ml of a $1.31 \times 10^{-5}M$ solution of MDH. To the solution was added 445µl of DMF at 15µl/min. The ester prepared above was added in 2µl aliquots and enzyme activity assayed after an interval of 5 minutes. In a first reaction 5µl of the ester was employed, while in a second reaction 9µl was added for a ratio of thyroxine to MDH of 4.1 and 7.4 respectively.

Both reaction mixtures were dialysed three times against 300ml 1M $K_2HPO_4$, pH 9.8, once against 300ml 0.05M carbonate buffer (pH 9.0) and then two times against the phosphate buffer. The two reaction mixtures were then chromatographed at 4° on a Sephadex G-50M column (0.9 × 54 cm) equilibrated with the phosphate buffer and eluted with the same phosphate buffer at a flow rate of 4 drops/min. and collected as 20 drop fractions. Active fractions were combined, the volume adjusted to 5ml with the phosphate buffer and a 0.5ml aliquot dialysed against 50ml aliquot deionized water at 4°. The radioactivity of an aliquot was determined and assuming no protein loss, the number of haptens per protein molecule was 2.0 and 3.0.

EXAMPLE VII $T_4$-MEMIDA Conjugate to Malate Dehydrogenase

Into 250µl of dry DMF was dissolved 10mg (11µmole) of $T_4$-MEMIDA and 1.3mg of N-hydroxysuccinimide. The reaction mixture was kept at 0° under a nitrogen blanket with stirring and 2.3mg ECDI was added and the mixture maintained at 0° until the ECDI had dissolved. The solution was allowed to stand at 4° overnight.

A generalized procedure for preparing the conjugate is provided, with greater or lesser hapten numbers, depending upon the amount of the $T_4$-MEMIDA hydroxysuccinimide ester employed in relation to the MDH. To 4ml of a stirring solution of MDH (pig heart, mitochondrial, Miles, 0.5mg/ml) in carbonate buffer, pH 9.2, was added one ml DMF. Successive additions of the $T_4$-MEMIDA ester were made at about 60 to 90 minute intervals and aliquots withdrawn and assayed for enzyme activity. The following table indicates the order of addition, the amount of the addition, the time of the addition, the ratio of added $T_4$ to MDH, and the percent deactivation observed. For conjugate number determinations, 2 to 20$\mu$l of the conjugation mixture was added to 0.5ml 1M potassium monoacid phosphate at 0°. For enzyme activity determinations, 2 to 20$\mu$l aliquots of the diluted conjugate was diluted to 0.8ml with 0.1 percent rabbit serum albumin in glycine buffer, 0.1M, pH 9.5, to which was added 100$\mu$l of 0.108M NAD and 100$\mu$l of 2M, pH 9.5 sodium malate. The rates were measured between 60 and 120 seconds after introduction at 30° in a Gilford Model 300-N spectrophotometer.

TABLE I

| Time | Addition $T_4$-ester $\mu$l | Total[1] Volume $\mu$l | $T_4$/MDH | $T_4$[2] Conj. | % Deactivation |
|---|---|---|---|---|---|
|  |  | 4996 | 0/1 |  | 0 |
| 10:34 | 13 | 5007 | 2/1 |  |  |
| 11:24 |  | 5003 | 2/1 |  | 30.1 |
|  | 1 ml withdrawn as conjugate c |  |  | 1.3 |  |
| 11:30 | 10.5 | 4011 | 4/1 |  |  |
| 12:03 |  | 4009 | 4/1 |  | 85.7 |
|  | 1 ml withdrawn as conjugate d |  |  | 2.8 |  |
| 1:10 | 8 | 3001 | 6/1 |  |  |
| 1:37 |  | 2991 | 6/1 |  | 94.0 |
|  | 1 ml withdrawn as conjugate e |  |  | 3.7 |  |
| 1:58 | 5.5 | 1977 | 8.1/1 |  |  |
| 2:49 | 4 | 1941 | 9.6/1 |  | 98.8 |
|  | 1 ml withdrawn as conjugate f |  |  | 5.6 |  |

[1]samples were periodically withdrawn and the enzyme activity determined which were not reported, which affect the total volume reported
[2]No. of $T_4$'s bound to MDH

EXAMPLE VIII $T_4$-MEMIDA Conjugate to Triose Phosphate Isomerase (TIM)

Into 500$\mu$l of dry DMF in a vial was introduced 6.0mg (6.8$\mu$mmoles) $T_4$-MEMIDA and 0.8mg (7.3$\mu$mmoles) N-hydroxy succinimide, the vial flushed with dry argon and covered, and the mixture cooled in an ice bath. To the stirred mixture was then added 1.5mg ECDI, the vial flushed with dry argon and stirred until everything dissolved. The vial was wiped dry, placed in covered plastic cup with Drierite $^R$, wrapped in foil and allowed to stand overnight at 4° with stirring.

To 1ml triose phosphate isomerase (2mg) in aqueous carbonate buffer (0.1M, pH 9.2) at 4°, 0.3ml DMF was added slowly with syringe. The ester solution was added slowly in increments by syringe and the enzyme activity monotored. When the enzyme was approximately 72% deactivated, DMF was added to bring the solution to 40% volume DMF.

The cold reaction mixture was passed through a Sephadex$^R$ G-25-(medium) column equilibrated with 0.1M carbonate buffer, pH 9.2. The column was a 50cc buret, 1.1cm in diameter with a bed volume of $\sim$19ml. The elution was carried out at 4° with a solution of 60 parts by volume of an aqueous solution 0.1M $CO_3$, pH 9.2 and 0.3M ammonium sulfate and 40 parts of DMF. Fractions were collected varying in volume from about 1 to 4ml. Fractions 5 and 6 were pooled (2.4ml) and dialysed first against $\sim$100ml aqueous 20 volume % DMF, 0.02M triethanolamine (TEA), pH 7.9, then 3 $\times$ 250ml aqueous 0.02 TEA, pH 7.9. The ratio of conjugated T-4 to enzyme was about 6.

EXAMPLE IX Desaminothyroxine conjugate to MDH

Desaminothyroxine (9.1 $\times$ 10$^{-3}$g. 1.2 $\times$ 10$^{-5}$mole) 1.4 $\times$ 10$^{-3}$g (1.2 $\times$ 10$^{-5}$mole) of NHS, and 0.25ml of dry DMF were successively added to a 1ml reaction vessel. The reaction mixture was cooled in an ice bath and 2.5 $\times$ 10$^{-3}$g (1.3 $\times$ 10$^{-5}$ mole) of ECDI added under a $N_2$ blanket. The reaction mixture was stirred overnight at 4°.

With cooling on an ice bath, and with stirring, DMF (0.23ml) was slowly added to 1.9 $\times$ 10$^{-3}$g (2.8 $\times$ 10$^{-8}$mole) of MDH in 0.83ml of 0.05M $NaNCO_3$-$Na_2$-$CO_3$ (pH b 9.00) with stirring while cooled in an ice bath. The above ester solution (5.8$\mu$l) was then added, with stirring and the stirring continued for one hour while maintaining the temperature. The conjugation mixture was gel filtered on three 0.9 $\times$ 13cm Sephadex$^R$ G-50M columns to yield a desaminothyroxine/MDH conjugate which was 91% deactivated and which had a hapten number of 2.5 (by iodine analysis). The conjugate enzyme activitiy was found to be 30% activated when treated with anti-$T_4$ sera.

EXAMPLE X $T_4$-MEMIDA Glycine

A 3ml Pierce Reacti-Vial$^{TM}$ was charged with 0.201g (2.18 $\times$ 10$^{-4}$mole) of $T_4$-MEMIDA and 0.025g (2.17 $\times$ 10$^{-4}$mole) of N-hydroxysuccinimide (NHS). Two ml of dry THF and 30$\mu$l (2.15 $\times$ 10$^{-4}$mole) of dry triethylamine were added and the reaction mixture was cooled to 0° with an ice bath. ECDI (0.048g, 2.50 $\times$ 10$^{-4}$mole) was added as a powder and the reaction mixture stirred for 35 minutes at 0°. The reaction mixture was then placed in the cold room (2°) and stirred for 15 hours. A TLC of the reaction mixture after 15 hours showed two spots with $R_1$ values of 0.06 ($T_4$-MEMIDA) and 0.60 ($T_4$-MEMIDA NHS ester), on an analytical silica gel plate, with 10% methanol in dichloromethane as the irrigant. A 25ml flask, equipped with stirring flea and septum stopper, was charged with 0.033g (4.39 $\times$ 10$^{-4}$mole) of glycine, followed by 1.50ml of distilled $H_2O$, 0.50ml of pyridine, and 100$\mu$l (1.00 $\times$ 10$^{-4}$mole) of 1.0N NaOH. The reaction mixture was cooled to 0° with an ice bath. With vigorous stirring, the $T_4$-MEMIDA NHS ester solution, prepared above, was added dropwise, and after addition the reaction mixture was placed in the cold room (2°) and stirred for 36 hours. The solvents were then stripped with a rotary evaporator to yield an oily pyridine-smelling solid. This solid was taken up in 10ml MeOH and poured into 15ml $H_2O$ and the solution was extracted with ethyl acetate (2 $\times$ 25ml). The combined organic layers were extracted once with 25ml of saturated brine, then dried over anhydrous $MgSO_4$. After filtration, the ethyl acetate was stripped on a rotary evaporator to yield a white crystalline solid. The solid was taken up in 2ml of methanol and put onto four preparative silica gel plates TLC plates, which were developed in triethylamine: methanol: dichloromethane (2.1: 10:90). The plates were run twice, then were scraped and the product deabsorbed with methanol: dichloromethane (1:1). The silica gel was filtered off and the filtrate reduced to 2ml in vacuo. A TLC of the product in THF showed only one spot with a $R_f$value of 0.50, on an analytical silica gel TLC plate, in triethylamine: methanol: dichloromethane (2.1:10:90). The product was recrystallized from THF/chloroform/cyclohexane.

EXAMPLE XI $T_4$-MEMIDA Glycylglycine

A 3ml Pierce Reacti-Vial$^{TM}$ was charged with 0.202g (2.20 $\times$ 10$^{-4}$mole) of $T_4$-MEMIDA, and 0.025g (2.17 $\times$ 10$^{-4}$mole) of NHS. Dry THF (2ml) and 31$\mu$l of dry triethylamine were added, and the reaction mixture was cooled to 0°. ECDI (0.051g, 2.66 × 10$^{-4}$mole) was added and the reaction mixture stirred in the cold room (2°) for 8.25 hours. A TLC indicated the formation of the T$_4$-MEMIDA NHS ester; R$_f$ value of 0.63, on an analytical silica gel plate, with triethylamine: methanol: dichloromethane (2.1:10:90). A 25ml flask, equipped with stirring flea and septum stopper, was charged with 0.058g (4.39 × 10$^{-4}$mole) of glycylglycine, followed by 1.50ml of H$_2$O and 0.50ml of pyridine and 100µl (1.0 × 10$^{-4}$mole) of 1.0N NaOH. The reaction mixture was cooled to 0°, and the T$_4$-MEMIDA NHS ester solution added dropwise with stirring. After addition of the activated ester, 1.0ml deionized H$_2$O and 0.50ml of pyridine was added. The reaction mixture was stirred in the cold room (2°) for 93 hours, worked up identical to that of T$_4$-MEMIDA glycine to yield 0.018g (9% yield) of a tan gold solid. The product was homogenous by TLC on silica gel with triethylamine: methanol: dichloromethane (2.1:10:80); R$_f$ value of 0.81, where the plate was developed twice.

EXAMPLE XII T$_4$-MEMIDA Glycine/MDH Conjugate

A 1ml Pierce Reacti-Vial$^{TM}$, equipped with stirring flea, was charged with 0.049g (5.0 × 10$^{-6}$mole) of T$_4$-MEMIDA and 39µl of dry DMF. The reaction mixture was cooled to 0° and 10µl (5.2 × 10$^{-6}$mole) of a 5.0 × 10$^{-1}$M NHS in DMF at 0° solution and 51µl (6.1 × 10$^{-6}$mole) of a 1.2 × 10$^{-1}$M ECDI in DMF solution at 0° were added and the reaction mixture stirred in the cold room (2°) for 49 hours. A TLC of the reaction mixture, after 49 hours, showed two spots with R$_f$ values of 0.49 (T$_4$-MEMIDA glycine) and of 0.68 (T$_4$-MEMIDA glycine NHS ester), on analytical silica gel plates, developed in triethyalmine: methanol: dichloromethane (2.1:10:90). MDH (4.0ml, 1.3 × 10$^{-5}$M, 0.05M NaHCO$_3$-Na$_2$CO$_3$, pH 9.2), was put into a 10ml round bottomed flask equipped with stirring bar and septum stopper, cooled to 0°, and the enzyme activity was determined, as described previously. Dry DMF (445µl) was added to the reaction mixture at a rate of 15µl per minute to yield a 10% DMF reaction mixture. The enzyme activity was again determined. The 4.3 × 10$^{-2}$M T$_4$-MEMIDA glycine NHS ester solution was added to the reaction mixture in 1 to 2µl aliquots, and the enzyme activity was determined after each addition. Nine microliters of the above activated ester solution gave an 82% deactivated enzyme conjugate. After the final addition of activated ester, the enzyme reaction mixture was exhaustively dialyzed against 1.0M K$_2$HPO$_4$(with 1.0 × 10$^{-3}$M NaN$_3$), at 2°. After dialysis, the enzyme conjugate was carefully removed from the dialysis bag and was passed through two Sephadex$^R$ G-50M (preswollen in 1.0M K$_2$HPO$_4$, with 1.0 × 10$^{-3}$M NaN$_3$) columns. The two column sizes were 0.9 × 54.0cm and 0.9 × 51.0cm, the flow rates were 4 to 5 drops per minute, and 20 drop fractions were collected. The protein fractions were concentrated using a collodion bag apparatus, in the cold room. The hapten number was determined to be 3.0.

EXAMPLE XIII T$_4$-MEMIDA glycylglycine/MDH Conjugate

ECDI (0.015g, 7.8 × 10$^{-5}$mole) was dissolved in 0.50 ml of dry DMF to yield a 1.6 × 10$^{-1}$M solution. NHS (0.75g, 6.5 ×10$^{-4}$ mole) was dissolved in 1.0ml of dry DMF to yield a 6.5 × 10$^{-1}$M solution. Both solutions were cooled to 0°, in an ice bath, prior to use. A 1ml Pierce Reacti-Vial$^{TM}$, equipped with stirring flea, was chaged with 2.4 × 10$^{-3}$g of T$_4$-MEMIDA glycylglycine, followed by 78µl of ice cold dry DMF, cooled in an ice bath, and then 4µl of a 6.5 × 10$^{-1}$M NHS in DMF solution at 0° and 18µl of a 1.6 × 10$^{-1}$M ECDI in DMF solution at 0° were added.

The reaction mixture was placed in the cold room (2°) and stirred for 20 hours. At the end of this time, a TLC of the reaction mixture showed two spots with R$_f$ values of 0.25 (T$_4$-MEMIDA glycylglycine) and of 0.59 (T$_4$-MEMIDA glycylglycine NHS ester), on analytical silica gel plates, developed in triethylamine: methanol: dichloromethane (2.1:10:90. MDH (4.0ml of a 1.5 × 10$^{-5}$M, 0.05M NaHCO$_3$-Na$_2$CO$_3$(pH 9.2)), was put into a 10ml round bottomed flask, equipped with stirring bar and septum stopper. The reaction mixture was cooled to 0°, with an ice bath, and 440µl of dry DMF was added at a rate of 50µl per minute. The enzyme activity was determined before and after the DMF addition. The 1.9 × 10$^{-2}$M T$_4$-MEMIDA glycylglycine NHS ester solution was added to the reaction mixture in 3 to 10µl aliquots and the enzyme activity was determined after each addition. The addition of 29 µl of the activated ester solution gave an 82% deactivated enzyme conjugate. The reaction mixture was then exhaustively dialyzed against 1.0M K$_2$HPO$_4$(with 1.0 ×10$^{-3}$M NaN$_3$), at 2°. After dialysis, the conjugate was passed through three Sephadex$^R$ G-50M columns (preswollen in 1.0M K$_2$HPO$_4$with 1.0 × 10$^{-3}$M, NaN$_3$) and was eluted with the same buffer. The column sizes were 0.9 × 55cm, 0.9 × 56cm, and 0.9 × 56cm, the flow rates were 4 to 5 drops per minute, and 20 drop fractions were collected. The protein fractions were concentrated using a collodion bag apparatus, in the cold room. The hapten number was determined to 3.9, by the method previously described.

Antibodies were prepared employing the antigen conjugates. Initially 2mg of the conjugate was injected. Then 0.25mg of the conjugate was injected at two week intervals. With sheep, the individual injection was a total of 2ml, of which 0.5ml was the conjugate dissolved in saline plus 1.5ml of Freund's complete adjuvant. 0.25ml aliquots were injected subcutaneously into each of 4 sites and 0.5ml aliquots were injected intramuscularly into each hind leg.

With rabbits, the total injection was 0.75ml, with 0.25mg of the conjugate dissolved in 0.25ml saline, and 0.5ml of Freund's complete adjuvant added. Injections of 0.09ml were injected subcutaneously into 4 sites and injections of 0.19ml injected into each hind leg.

The animals are normally bled about 5 to 7 days after each injection and the antibodies isolated according to conventional procedures.

To demonstrate the utility of the thyroxine-MDH conjugate for assaying for T$_4$, a number of assays were carried out. In a first series of assays, the assays were carried out with varying amounts of antibody to demonstrate the increase in activity of the enzyme conjugate with increasing amounts of antibody. In a second series of assays, varying amounts of T$_4$ were added to antibody, so as to change the effective concentration of antibody which is available for binding to the MDH-bound-thyroxine. From these results it is shown, that by establishing a standard curve based on samples containing known amounts of thyroxine, one can determine the amount of thyroxine which is free in serum by relating the observed values of the enzyme activity to the standard curve.

The assay procedure is as follows. A 0.8ml solution of 0.1 weight percent RSA in 0.1M glycinate buffer, pH 9.5, containing $10^{-3}$M EDTA, is prepared of the anitbody solution, and the MDH-bound-T-4. The solution is incubated for 45 minutes, at which time the substrates (100µl 2M malate and 100µl 0.108M NAD) are added and the solution is transferred to a spectrophotometer and the values read at 30°, as the change in optical density between 120 seconds and 60 seconds from the introduction into the spectrophotometer. For the conjugates prepared in Example VII, employing sheep anitbody, the following table indicates the results.

TABLE II

| $Ab_{T-4}$[1] µl | Conjugate Example VII | | | |
|---|---|---|---|---|
| | $c^2$ % change | $d^2$ % change | $e^2$ % change | $f^2$ % change |
| 0 | — | — | — | — |
| 1 | +17 | 113 | 246 | 34 |
| 2 | +17 | 124 | 358 | 111 |
| 3 | +17 | 130 | 389 | 190 |
| 4 | +17 | 126 | 399 | 290 |
| 5 | +17 | 129 | 427 | 376 |
| 10 | +17 | 130 | 467 | 665 |
| 15 | +17 | 136 | 471 | 725 |
| 20 | +17 | 139 | 503 | 829 |
| 25 | +17 | 144 | 485 | 825 |

[1] ~$9.0 \times 10^{-6}$M $Ab_{T-4}$ based on binding sites; $K = 1.12 \times 10^9$
[2] Concentration (M) of enzyme
c — $5 \times 10^{-10}$
d — $2.56 \times 10^{-9}$
e — $1.4 \times 10^{-8}$
f — $3.7 \times 10^{-8}$ A series of assays were now carried out, whereby a thyroxine solution of 9.7mg in 25ml of 0.05N sodium hydroxide was serially diluted with 0.05N sodium hydroxide. The assays were carried out by combining 600µl of 0.1% rabbit serum albumin, 100µl of antibody of 0.1M glycine buffer, pH 9.5, $10^{-3}$M EDTA and 100µl of the $T_4$ solution and the mixture incubated for 15 minutes at room temperature. To the solution was then added a specified voume of the MDH-bound-T-4 solution and the mixture incubated for 10 minutes. The substrates were then added and readings were taken in a spectrophotometer at 30° as indicated previously. The following table indicates the results.

TABLE III[3]

| $T_4$ Sample conc, M | Conjugate[1,2] | | |
|---|---|---|---|
| | c ΔOD | d ΔOD | e ΔOD |
| — | 91 | 81 | 248 |
| $5 \times 10^{-10}$ | 89 | 83 | 254 |
| $5 \times 10^{-9}$ | 88 | 82 | 255 |
| $5 \times 10^{-8}$ | 90 | 81 | 249 |
| $5 \times 10^{-7}$ | 88 | 77 | 212 |
| $5 \times 10^{-6}$ | 95 | 54 | 93 |
| $5 \times 10^{-5}$ | 99 | 56 | 85 |

[1] volume of enzyme conjugate employed and concentration
c — 15µl  $1.11 \times 10^{-7}$M
d — 5µl  $5.12 \times 10^{7}$M
e — 5µl  $2.81 \times 10^{-6}$M
[2] anti-thyroxine $9 \times 10^{-6}$M in binding sites diluted 1 to 33 prior to addition in 100µl
[3] ΔOD × $10^3$ Following the procedure described in Example VII, another conjugate was prepared which was chromatographed on a Sephadex G-50 column which had been equilibrated with 1M potassium monoacid phosphate. The flow was slow and 20 drop fractions were collected until tube 39, after which time 99 drop fractions were collected. The process was repeated with a second G-50 column, each time concentrating the collected fractions with Sephadex G-200 by ultrafiltration. By analysis, the number of T-4 groups per enzyme was determined to be from 4.3 to 5.3, average 4.8.

A series of assays were carried out using various sources of anti-serum and varying concentrations of thyroxine. As described in the previous procedure, the antibody and thyroxine were combined in a 0.1 percent glycine buffered RSA solution and incubated 15 minutes, followed by the addition of the indicated amount of enzyme solution, the assay mixture incubated for an additional 10 minutes, the substrates added, and then introduced into a spectrophotometer, the second minute being read as to the change in optical density units. The volume of antibody added is one µl and the volume of enzyme added is one µl. The following table indicates the results.

TABLE IV[1]

| $T_4$ Assay conc. M | Antisera | | |
|---|---|---|---|
| | A ΔOD | B ΔOD | C ΔOD |
| — | 76 | 61 | 87 |
| $5 \times 10^{-5}$ | 20 | 24 | 26 |
| $5 \times 10^{-6}$ | 28 | 29 | 29 |
| $5 \times 10^{-7}$ | 30 | 39 | 32 |
| $5 \times 10^{-8}$ | 38 | 50 | 62 |
| $5 \times 10^{-9}$ | 73 | 59 | 84 |
| $5 \times 10^{-10}$ | 81 | 61 | 94 |
| $5 \times 10^{-11}$ | 78 | 63 | 92 |

[1] ΔOD × $10^3$

In carrying out the T-4 Assay employing TIM-T-4 conjugate, the following reagents were employed.

TIM-T-4 Assay Reagents

Buffer: 0.02M triethanolamine (TEA)-HCl, pH, 7.9; 10 0.0054M ethylene diamine tetraacetic acid (EDTA).
Rabbit serum albumin solution: 0.2 wt. % RAS, in buffer.
TIM-T-4 solution: ~$7 \times 10^{-3}$ µM of T-4, as TIM-T-4, in RSA solution (provides assay rate of ~200 OD/min)
Anti-T-4 solution: ~$4 \times 10^{-5}$M anti-T-4 based on binding sites in RSA solution.
NADH solution: 2.5 mg NADG/ml in buffer (stock solution) prepared according to TEKIT instructions and diluted 1:7 parts by weight with buffer.
DL-glyceraldehyde-3-phosphate solution (GAP): Prepared from CL-glyceraldehyde-3-phosphate diethylacetal, Ba salt from Sigma Chemical Co., St. Lousi, Mo., 1.5g of salt treated to give final volume of 10ml.
α-glycerophosphate dehydrogenase (α-GPDH) solution: 0.2m/ml in buffer (Boehringer-Mannheim).
Thyroxine (T-4 solution): $2.57 \times 10^{-4}$M in RSA solution. The assay was carried out as follows. A number of dilutions of the T-4 solution were prepared. Initially, 0.4 ml of the T-4 solution, 0.4ml of the TIM-T-4 solution and 0.4ml of the antibody solution were mixed, and set in a 30° water bath for 12 minutes. To the solution was then added 200µl of the NADH solution, 25µl of the alpha-GPDH solution and 100µl of the GAP solution. The assay tube was covered with parafilm and an aliquot was then aspirated into a thermocuvette in a 300N Gilford Spectrophotometer and the first reading made after 30 seconds while in the machine at 30° C. The optical density was read at 366nm at 30° C. The remainder of the assay solution was maintained in a 30° C bath and read after 13 minutes. The following table indicates the results.

TABLE V

| Sample No. | T-4 Soln. Conc. | Decrease in OD in 13' |
|---|---|---|
| 1 | 0 | 0.543 |
| 2 | $3.84 \times 10^{-6}$ | 0.550 |
| 3 | $7.68 \times 10^{-6}$ | 0.550 |
| 4 | $1.54 \times 10^{-5}$ | 0.490 |
| 5 | $6.14 \times 10^{-5}$ | 0.448 |
| 6 | $1.29 \times 10^{-4}$ | 0.422 |
| 7 | $5.14 \times 10^{-4}$ | 0.409 |

The results of the foregoing tables demonstrate that extrememely low concentrations, as well as extremely small amounts of thyroxine can be detected by the subject method. The method is quite straight forward in requiring few manipulative steps. By combining the reagents in a buffered medium, and optionally incubating the mixture, followed by the addition of the enzyme substrates, one can determine T-4 by a spectrophotometric reading over a short period of time. The system allows for automation, so that samples and reagents can be mixed automatically and read.

Although the foregoing invention has been described in some detail by way of illustration and example for purposes of clarity of understanding, it will be obvious that certain changes and modifications may be practiced within the scope of the appended claims.

What is claimed is:

1. A method for determining the presence of thyroxine in a medium suspected of containing said thyroxine, which comprises:
    bringing together in an aqueous liquid zone: (1) said medium; (2) soluble ENZ-bound-thyroxine; and (3) antithyroxine, said antithyroxine having sites common to and capable of binding to said thyroxine and said ENZ-bound-thyroxine, wherein ENZ is an enzyme selected from malate dehydrogenase or tricore phosphate isomerase and both of which are reversibly inhibited by said thyroxine and said antithyroxine is present at a concentration resulting in substantial enhancement of said enzyme activity in the absence of thyroxine; and
    analyzing in said zone for the effect of said medium on the enzymatic activity of said ENZ-bound-thyroxine.

2. A method according to claim 1, wherein ENZ is malate dehydrogenase to form MDH-bound-thyroxine.

3. A method according to claim 1, where ENZ is triose phosphate isomerase.

4. A method according to claim 1, wherein said aqueous liquid zone is buffered at a pH in the range of about 7 to 10.5, and said ENZ-bound-thyroxine has less than about 50 percent of the enzyme activity of the ENZ prior to conjugation to form ENZ-bound-thyroxine, but not less than about 0.5 percent of the enzyme activity of said ENZ prior to conjugation.

5. A method according to claim 4, wherein ENZ is malate dehydrogenase and said enzymatic activity is determined by the addition of NAD and malate to said aqueous liquid zone at a pH in the range of 8.5 to 10.5.

6. A method according to claim 4, wherein ENZ is triose phosphate isomerase and said enzymatic acitivty is determined by the addition of glyceraldehyde-3-phosphate,α-glycerophosphate dehydrogenase and NADH to said aqueous liquid zone at a pH in the range of 7 to 9.

7. A method according to claim 2, wherein said medium and said antithydroxine are combined prior to the addition of said MDH-bound-thyroxine.

8. A method according to claim 2, wherein said MDH-bound-thyroxine has from about 1 to 10 thyroxine per MDH, said MDH is mitochrondial MDH and is deactivated to the extent of from about 65 to 99.5 percent of the enzyme activity of the MDH prior to conjugation to form MDH-bound-thyroxine.

9. A method according to claim 2, wherein the MDH in said MDH-bound-thyroxine is derived from mitochrondial MDH.

10. A method for determining the presence of thyroxine in a medium suspected of containing said thyroxine, which comprises:
    bringing together in an aqueous buffered liquid zone at a pH in the range of 6-10.5: (1) said medium; (2) ENZ-bound-thyroxine; (3) antithydroxine, said antithyyroxine having sites common to and capable of binding to said thyroxine and said ENZ-bound-thyroxine, wherein ENZ is malate dehydrogense reversibly inhibited by said thyroxine, and said antithydroxine is present at a concentration resulting in substantial enhancement of said enzyme activity in the absence of thyroxine; and
    analyzing in said zone and NAD or NADH for the effect of said medium on the enzymatic activity of said ENZ-bound-thyroxine.

11. A method according to claim 10, wherein said analyzing is with NAD and malate.

12. A method according to claim 11 wherein said medium and said antithyroxine are brought together, followed by said ENZ-bound-thyroxine.

* * * * *